United States Patent [19]

Kamiya et al.

[11] 4,110,338
[45] Aug. 29, 1978

[54] PRODUCT AND PREPARATION OF 1H-TETRAZOLE-5-THIOL DERIVATIVES

[75] Inventors: Takashi Kamiya, Suita; Kunihiko Tanaka, Toyonaka; Youichi Shiokawa, Takatsuki, all of Japan

[73] Assignee: Fujisawa Pharmaceutical Co., Ltd., Osaka, Japan

[21] Appl. No.: 518,956

[22] Filed: Oct. 29, 1974

[30] Foreign Application Priority Data

Oct. 31, 1973 [JP] Japan .................................. 48-123118
Jun. 19, 1974 [JP] Japan .................................. 49-70440

[51] Int. Cl.² .................... C07D 257/04; A61K 31/54
[52] U.S. Cl. ................................. 260/308 D; 424/246
[58] Field of Search .................................... 260/308 D

[56] References Cited

U.S. PATENT DOCUMENTS

| 3,437,665 | 4/1969 | Maggiulli et al. ............... 260/308 D |
| 3,557,285 | 1/1971 | Enkoji et al. .................... 260/308 D |
| 3,639,417 | 2/1972 | Porter et al. ..................... 260/308 D |

OTHER PUBLICATIONS

*Berichte*, 28, (1895), pp. 74–81.
*Chemical Abstracts* vol. 24, 2748, (1930); vol. 55, (1961), 14441–14442; vol. 63, 11544, (1965); vol. 71, 38871p (1969).

*Primary Examiner*—Frederick E. Waddell
*Attorney, Agent, or Firm*—Dayton R. Stemple, Jr.

[57] ABSTRACT

The process for preparation of and the intermediate compounds such as 1H-tetrazole-5-thiol having the formula

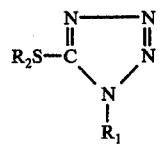

wherein $R_1$ is alkyl, aminoalkyl, acylaminoalkyl, aryl, alkoxycarbonylaminoalkyl, halogen-substituted aryl or alkylamino-substituted aryl and $R_2$ is hydrogen or aralkyl, preferably benzyl. The compound is produced by reacting a substituted thiosemicarbazide with an aralkyl chloride, subjecting the resultant compound to diazotization, and reacting the resultant compound with a Friedel Crafts catalyst. Optionally, this may be further hydrolyzed when $R_1$ is aminoalkyl and/or converted to conventional salts.

7 Claims, No Drawings

PRODUCT AND PREPARATION OF 1H-TETRAZOLE-5-THIOL DERIVATIVES

This invention relates to a process for the preparation of 1H-tetrazole-5-thiol derivatives. It particularly relates to a process for preparing 1H-tetrazole-5-thiol derivatives represented by the formula:

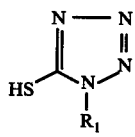
(I)

wherein R is alkyl, aminoalkyl, acylaminoalkyl, aryl, alkoxycarbonylaminoalkyl, halogen-substituted aryl or alkylamino-substituted aryl.

The invention also relates to a new key intermediate obtained in the process of this invention and represented by the formula:

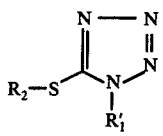

wherein $R_1'$ is the same as $R_1$ defined above and $R_2$ is aralkyl, preferably benzyl.

The 1H-tetrazole-5-thiol derivatives (I) prepared by the process of this invention include both new and known compounds and can be prepared by the following new process which comprises reacting a substituted thiosemicarbazide of the formula:

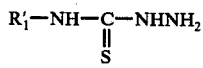
(II)

wherein $R_1'$ is alkyl, acylaminoalkyl, aryl, halogen-substituted aryl or alkylamino-substituted aryl, with a compound of the formula:

(III)

wherein $R_2$ is aralkyl and X is a residue of an acid, to give a N,S-disubstituted thiosemicarbazide of the formula:

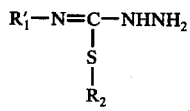
(IV)

wherein $R_1'$ and $R_2$ are each as defined above, subjecting the resultant compound (IV) to diazotization to give a 5-aralkylthio-1H-tetrazole of the formula:

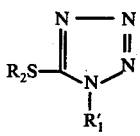
(V)

wherein $R_1'$ and $R_2$ are each as defined above, and reacting the resultant compound (V) with a Friedel Crafts' catalyst to give the compound of the formula:

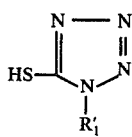
(I')

wherein $R_1'$ is as defined above, and, when desired, followed by hydrolyzing the resultant compound (I') wherein $R_1'$ is acylaminoalkyl to give the 1-aminoalkyl-1H-tetrazole-5-thiol of the formula:

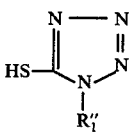
(I'')

wherein $R_1''$ is aminoalkyl, and further, when desired, reacting the resultant compound (I'') with a reagent being capable of introducing an alkoxycarbonyl group on the amino group to give a compound of the formula:

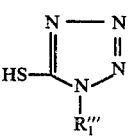
(I''')

wherein $R_1'''$ is alkoxycarbonylaminoalkyl.

Thus obtained 1H-tetrazole-5-thiol derivative (I) can be converted according to a conventional manner into its salt.

As used herein, the term "alkyl" includes an alkyl group of a straight or branched carbon chain, preferably lower alkyl having 1 to 6 carbon atoms(s) such as methyl, ethyl, propyl, isopropyl, butyl, isobutyl, t-butyl, pentyl or hexyl and a cycloalkyl group, preferably a lower cycloalkyl having 5 or 6 carbon atoms such as cyclopentyl or cyclohexyl; "alkyl" of the aminoalkyl, acylaminoalkyl and alkoxycarbonylaminoalkyl groups may be an alkyl group of a straight or branched carbon chain, preferably lower alkyl having 2 to 6 carbon atoms such as ethyl, propyl, isopropyl, butyl, isobutyl, t-butyl, pentyl, hexyl, "aminoalkyl" may be preferably amino(lower)alkyl having 2 to 6 carbon atoms such as aminoethyl, aminopropyl, aminoisopropyl, aminobutyl, aminoisobutyl, amino-t-butyl, aminopentyl or aminohexyl; "acylaminoalkyl" means N-acylated aminoalkyl, of which the aminoalkyl group is to be referred to one mentioned above and the acyl group includes alkanoyl, preferably lower alkanoyl having 1 to 7 carbon atom(s) such as formyl, acetyl, propionyl, butyryl, isobutyryl, valeryl or caproyl, aroyl such as benzoyl, toluoyl or xyloyl, and heterocyclic-carbonyl such as nicotinoyl, thenoyl or furoyl, and "alkoxycarbonylaminoalkyl" means the aminoalkyl group as mentioned above whose amino group is substituted with "alkoxycarbonyl", preferably lower alkoxycarbonyl having 2 to 7 carbon atoms such as methoxycarbonyl, ethoxycarbonyl, propoxycarbonyl, butoxycarbonyl, t-butoxycarbonyl, pentyloxycarbonyl or hexyloxycarbonyl, and "alkoxycarbonylaminoalkyl" may be methoxycarbonylaminoethyl, ethoxycarbonylaminoethyl, propoxycarbonylaminoethyl or t-butoxycarbonylaminoethyl; "aryl" includes phenyl or alkyl-substituted aryl such as alkyl-substituted phenyl wherein the alkyl group may be an alkyl group of a straight or branched carbon chain, preferably having 1 to 6 carbon atom(s) as mentioned above, and the alkyl-substituted aryl group may be tolyl, xylyl, mesityl or cumenyl; "halogen" means fluorine, chlorine, bromine or iodine; "alkylamino-substituted aryl" may be the aryl group mentioned above which is substituted with alkylamino, preferably lower alkylamino having 1 to 6 carbon atom(s) such as mono(-lower)alkylamino (e.g. methylamino, ethylamino or propylamino) or di(lower)alkylamino (e.g. dimethylamino, diethylamino or methylethylamino); and aralkyl may be proferably aryl(lower)alkyl, more preferably α-aryl-substituted lower alkyl wherein the aryl group may be referred to one mentioned above and the alkyl group may be referred to that of the alkyl-substituted aryl group as mentioned above, and the aralkyl group may be benzyl, 1-phenethyl, tolylmethyl, xylylmethyl or naphthylmethyl; "the residue of an acid" may be a residue of hydrohalogenic acid such as hydrochloric acid, hydrobromic acid or hydroiodic acid, sulfuric acid, alkylsulfuric acid, benzenesulfonic acid, toluenesulfonic acid, dialkylcarbamic acid and the like, and the salt of the compound (I) may be an acid addition salt, of an organic or inorganic acid (e.g. hydrochloride, hydrobromide, sulfate, nitrate, phosphate, succinate tartrate, citrate and the like) when $R_1$ is aminoalkyl and a salt with a base such as alkali or alkaline earth metal hydroxides, carbonates and bicarbonates such as sodium, potassium, magnesium, calcium, hydroxides, carbonates, and bicarbonates.

In the new process of this invention the first step comprises the reaction of a substituted thiosemicarbazide (II) with a compound (III).

The reaction may be usually carried out in an inert solvent such as acetone, dioxane, methanol, ethanol, ether, acetonitrile, chloroform, methylene chloride, ethylene chloride, tetrahydrofuran, ethyl acetate, dimethylformamide, pyridine, and the like. There is no limitation in the reaction temperature and it may be usually carried out at room temperature or at an elevated temperature in accordance with the kinds of the starting material (II) and the compound (III) to be employed. The resultant product (IV) may be isolated from the reaction mixture and purified in a conventional manner and also can be used in the subsequent step without any isolation or purification.

Thus obtained N,S-disubstituted thiosemicarbazide (IV) is then subjected to diazotization to give the 5-aralkylthio-1H-tetrazole (V). The diazotization is usually carried out by reacting the compound (IV) with a diazotizating agent such as nitric oxide, nitrous acid or nitrous acid derivative. The nitrous acid derivative may be an alkyl nitrite such as methyl nitrite, ethyl nitrite, amyl nitrite, isoamyl nitrite, nitrosyl chloride, nitrosyl sulfate or nitrosyl acetate. Nitrous acid may be also used in a form of an alkali metal salt such as sodium nitrite or potassium nitrite, conventionally in the presence of an inorganic or organic acid, such as hydrochloric acid, sulfuric acid, acetic acid or trifluoroacetic acid.

In this process, there may be different methods of diazotization in accordance with a reagent used. Typical methods are given below. When nitric oxide is used as a reagent, the reaction is usually carried out by bubbling its gas through a solution of the compound (IV). When a nitrite is used, the reaction is usually carried out by adding under ice-cooling an aqueous solution of the nitrate into a solution of the compound (IV) in an inorganic acid such as hydrochloric acid, sulfuric acid or nitric acid, or an organic acid such as formic acid or acetic acid. When an alkyl nitrite or a nitrosyl compound is used, the reaction is usually carried out by adding an alkyl nitrite or a nitrosyl compound into a solution of the compound (IV) in an organic acid such as formic acid or acetic acid. Usually, nitrosyl sulfate is used in sulfuric acid and nitrosyl acetate is in acetic acid, most conventionally. All these methods may be usually carried out at room or lower temperatures.

The resultant product (V) may be isolated from the reaction mixture and purified in a conventional manner and also can be used in the subsequent step without isolation or purification.

The 1H-tetrazole derivative (V) obtained above is treated with a Friedel Crafts' catalyst to give the compound (I'). The Friedel Crafts' catalyst employed in this reaction means Lewis acid used as a condensing agent in so-called Friedel Crafts' reaction, and its suitable example may be boron trihalide such as boron trichloride or boron tribromide; an aluminum trihalide such as aluminum trichloride or aluminum tribromide; zinc chloride; sulfuric acid and other condensing agent usually employed in the Friedel Crafts' reaction.

This reaction is usually carried out in an organic solvent such as methylene chloride, chloroform, benzene, tetrahydrofuran, dimethylformamide, toluene, xylene or an other solvent inert to the reaction or a mixture thereof. The reaction temperature is not particularly limited, and is usually room or elevated temperature. The resultant product (I') is isolated and purified in the usual manner.

The compound (I') wherein $R_1'$ is acylaminoalkyl can be further hydrolyzed, when desired, to give the compound (I"). The hydrolysis is advantageously carried out by heating the compound (I') wherein $R_1'$ is acylaminoalkyl or its salt in an aqueous solution of a base such as sodium hydroxide, potassium hydroxide, sodium carbonate, potassium carbonate or of an inorganic acid such as sulfuric acid or hydrochloric acid.

Furthermore, the resultant compound (I") can be reacted, when desired, with a reagent being capable of introducing an alkoxycarbonyl group on the aminoalkyl group to give the compound (I''').

As the reagent being capable of introducing an alkoxycarbonyl group on the aminoalkyl group to be used in this reaction may be alkoxycarbonyl azide, alkyl chloroformate, dimethyl 2-alkoxycarbonyloxyimino malonate and other reagent usable conventionally for converting an aminoalkyl group to an alkoxycarbonylaminoalkyl group by introducing an alkoxycarbonyl group on an aminoalkyl group.

The reaction is preferably carried out in the presence of a base such as triethylamine or tetramethylguanidine, usually in a mixed solvent of water and a solvent miscible with water. The reaction temperature may be desirably selected depending upon the reactants being used.

The compounds (I) and their salts prepared by the process of this invention are useful as intermediates for the preparation of the cephalosporin derivative having antibiotic activity, for example, represented by the formula:

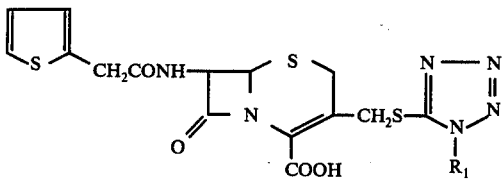

wherein $R_1$ is defined above, which can be prepared by reacting 7-(2-thienylacetamido)cephalosporanic acid with the compound (I) provided by this invention.

The present invention is illustrated by the following examples, but not limited thereto.

EXAMPLE 1

(1) 4-Methylthiosemicarbazide (3.15 g.) and benzyl chloride (4.175 g.) were added to ethanol (30 ml.) and the mixture was heated under reflux for 2 hours. After the solvent was removed under reduced pressure, the residue was dissolved in methanol (3 ml.) under warming. Ether (10 ml.) was added to the resultant solution and the mixture was shaken. Methanol (3 ml.) was added dropwise thereto under stirring to obtain a homogeneous solution and the solution was allowed to stand at room temperature. The appearing precipitates were collected by filtration and washed with ether to give S-benzyl-4-methylthiosemicarbazide hydrochloride (4.707 g.), m.p. 139.5° to 141° C.

The filtrate was concentrated under reduced pressure and the obtained residue was recrystallized from a mixed solution of methanol and ether (1:4) to give also the object compound (1.567 g.). Total yield : 6.274 g.

I.R. spectrum (Nujol)
 $\nu$ (cm$^{-1}$) : 3150, 1645, 1590
N.M.R. spectrum (in D$_2$O)
 $\delta$ (ppm) 3.04 (3H, s)
  4.42 (2H, s)
  7.48 (5H, s)

(2) To a solution of S-benzyl-4-methylthiosemicarbazide hydrochloride (1.158 g.) in water (10 ml.) was added dropwise a solution of sodium nitrite (0.345 g.) in water (2 ml.) under stirring at 15° to 20° C over 5 minutes. To the mixture was added dropwise 10% hydrochloric acid (2 ml.) at 10° to 15° C with stirring over 20 minutes and then further stirred at 10° C for 30 minutes. The appearing precipitates were collected by sucked filtration and washed with cold water to give 1-methyl-5-benzylthio-1H-tetrazole (0.957 g.). The product was recrystallized from a mixture of ether and n-hexane to give the purified object compound, m.p. 48.5° to 49.5° C.

I.R. spectrum (Nujol)
 $\nu$ (cm$^{-1}$) : 770, 690
N.M.R. spectrum (in CDCl$_3$)
 $\delta$ (ppm) 3.75 (3H, s)
  4.49 (2H, s)
  7.29 (5H, m)

(3) A mixture of 1-methyl-5-benzylthio-1H-tetrazole (2.06 g.), aluminum chloride (2.003 g.) and toluene (10 ml.) was heated under reflux with stirring for 20 minutes. Water (20 ml.) was added thereto gradually under ice cooling in order to decompose excess aluminum chloride. Toluene (15 ml.) was further added thereto and the aqueous layer was separated off. The toluene layer was extracted twice with water (15 ml. and 10 ml.). The aqueous layers were combined together and concentrated under reduced pressure, and the residue was extracted four times with hot chloroform (25 ml.). The chloroform extract was dried over magnesium sulfate, and the chloroform was removed under reduced pressure to give 1-methyl-1H-tetrazole-5-thiol (1.012 g.). The product was recrystallized from chloroform (2 ml.) to give the purified object compound, m.p. 123.5° to 124° C.

I.R. spectrum (Nujol)
 $\nu$ (cm$^{-1}$) : 3200-2600, 1510

EXAMPLE 2

A mixture of 4-methylthiosemicarbazide (21 g.), benzyl chloride (27.83 g.) and ethanol (150 ml.) was heated under reflux for 2 hours and the solvent was removed under reduced pressure. The residue was dissolved in water (120 ml.), the aqueous solution (23 ml.) containing sodium nitrite (13.8 g.) was added thereto over 15 minutes with stirring at 10° to 15° C, and then 10% hydrochloric acid (73 ml.) was added thereto at the same temperature over 40 minutes. The mixture was stirred for 20 minutes and extracted with toluene (150 ml. and 50 ml.). The extract was dried over magnesium sulfate and then filtered. The magnesium sulfate was washed two times with toluene (15 ml.) and then the washings and the filtrate were combined together. The mixed solution was concentrated to the volume of about 120 ml under reduced pressure and then, to the concentrate, was added powder of aluminum chloride (33.375 g.). The resultant mixture was heated under reflux for 15 minutes with stirring and water (150 ml.) was added bit by bit to the reaction mixture under ice cooling and then toluene (30 ml.) was added thereto. The toluene layer was separated out from the aqueous layer and washed two times with water (50 ml.). The aqueous layer and the washings were combined together and extracted with toluene (20 ml.). The above obtained toluene solution and the extract were combined together and extracted with 20% aqueous solution (10 ml.) of sodium hydroxide. The extract was washed with toluene (5 ml.) and adjusted to pH 1 with concd. hydrochloric acid under ice cooling. The appearing crystals were filtered by suction, dried and then recrystallized from ethyl acetate (3 ml.) to give 1-methyl-1H-tetrazole-5-thiol (918 mg.), m.p. 122° to 124.5° C. The aqueous solution left after the extraction with toluene (20 ml.) was saturated with sodium chloride and extracted twice with ethyl acetate (100 ml.) and once with ethyl acetate (50 ml.). The extracts were combined and dried over magnesium sulfate. To the solution containing magnesium sulfate was added activated charcoal (1.5 g.) and the mixture was shaken for about 5 minutes and then filtered. The residue was washed with ethyl acetate (30 ml.), and the washing was combined with the ethyl acetate filtrate. The solution was concentrated to the volume of 20 to 25 ml. under reduced pressure, heated to dissolve the appearing crystals and then allowed to stand at room temperature. The appearing crystals were filtered and washed with ethyl acetate (3 ml.) to give 1-methyl-1H-tetrazole-5-thiol (8.517 g.), m.p. 122.5° to 125° C. The filtate was concentrated to volume of about 10 ml., heated to dissolve the appearing crystals and then allowed to stand at room temperature. The appearing crystals were filtered by suction and washed with ethyl acetate (2 ml.) to give the object compound (4.303 g.). The filtrate was concentrated under reduced pressure and the residue was dissolved in ethyl acetate under heating and the solution was allowed to stand at room temperature. The precipitates were filtered by suction and washed with cold ethyl acetate to give the object compound (1.781 g.). Total yield : 15.519 g.

U.V. spectrum
 $\lambda_{max}^{Ethanol}$ 247 mμ, $\lambda_{max}^{H_2O}$ 224 mμ.
I.R. spectrum (Nujol)
 $\nu$ (cm$^{-1}$) : 3200–2600, 1510
N.M.R. spectrum (in DMSO-d$_6$)
 $\delta$ (ppm) : 3.66 (3H, s)

EXAMPLE 3

The following compounds were obtained from the corresponding starting compounds, in similar manners to those of Examples 1 and 2.

(1) 1-Ethyl-1H-tetrazole-5-thiol
 m.p. 48° to 50° C (dec.)
 U.V. spectrum
  $\lambda_{max}^{H_2O}$ 225 mμ
(2) 1-Propyl-1H-tetrazole-5-thiol
 m.p. 60° to 65° C
 U.V. spectrum
  $\lambda_{max}^{H_2O}$ 225 mμ
(3) 1-Butyl-1H-tetrazole-5-thiol
 m.p. 36° to 38° C
 U.V. spectrum
  $\lambda_{max}^{H_2O}$ 225 mμ
(4) 1-Cyclohexyl-1H-tetrazole-5-thiol
 m.p. 84° to 87° C
 U.V. spectrum
  $\lambda_{max}^{H_2O}$ 230 mμ
(5) 1-Acetamidoethyl-1H-tetrazole-5-thiol
 m.p. 137.5° to 139.5° C
(6) 1-Phenyl-1H-tetrazole-5-thiol
 m.p. 155° C
(7) 1-(o-Tolyl)-1H-tetrazole-5-thiol
 m.p. 109° to 115° C
(8) 1-(4-Chlorophenyl)-1H-tetrazole-5-thiol
 m.p. 178° C
(9) 1-(4-Dimethylaminophenyl)-1H-tetrazole-5-thiol
 m.p. 179° C (dec.)

EXAMPLE 4

A mixture of 1-(2-acetamidoethyl)-1H-tetrazole-5-thiol (1.56 g.) in 6N-hydrochloric acid (20 ml.) was heated under reflux for 2 hours and the resulting solution was evaporated to dryness under reduced pressure. The residue was dried over potassium hydroxide under reduced pressure to give 1-(2-aminoethyl)-1H-tetrazole-5-thiol hydrochloride (1.45 g.), m.p. 190° to 193° C (dec.).

EXAMPLE 5

To a solution of 1-(2-aminoethyl)-1H-tetrazole-5-thiol hydrochloride (1.82 g.), t-butoxycarbonylazide (2.86 g.), water (20 ml.) and dioxane (20 ml.) was added triethylamine (6.0 g.), and the mixture was stirred at room temperaure for 1 hour. After dioxane was removed therefrom under reduced pressure, the residue was adjusted to pH 7.5 to 8.0 with 5% aqueous solution of sodium bicarbonate and washed twice with ether. The resultant solution was adjusted to pH 1 with 5% hydrochloric acid and extracted three times with ethyl acetate (each 50 ml.). The extract was washed with an aqueous saturated solution of sodium chloride, dried over magnesium sulfate and then concentrated under reduced pressure to give 1-(2-t-butoxycarbonylaminoethyl)-1H-tetrazole-5-thiol (2.05 g.), m.p. 117° to 120° C. (dec.).

I.R. spectrum (Nujol)
 $\nu$ (cm$^{-1}$) : 3260, 3100, 1670

What is claimed is:
1. A process for the preparation of a 1-substituted 1H-tetrazole-5-thiol of the formula:

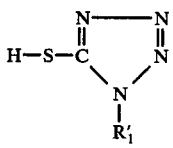
(I)

which comprises reacting at elevated temperature a substituted thiosemicarbazide of the formula:

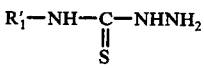
(II)

with a compound of the formula:

$R_2$—X   (III)

to give a N,S-disubstituted thiosemicarbazine of the formula:

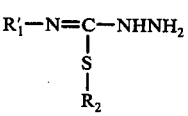
(IV)

subjecting at lower temperature the resultant compound (IV) to diazotization to give a 5-aralkylthio-1H-tetrazole of the formula:

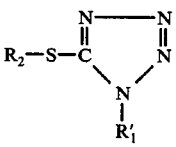
(V)

and reacting at elevated temperature the resultant compound (V) with a slightly molar excess of Friedel Crafts' catalyst to give a compound of the formula:

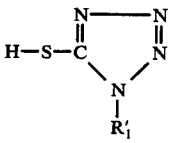
(I')

and when desired, converting the resultant compound (I') into its salt, wherein
 $R_1'$ is alkyl of 1–6 carbon atoms
 $R_2$ is aralkyl, and
 X is a residue of an acid.
2. The process of claim 1 wherein
 $R_2$ is phenylethyl
 X is halogen.

3. The process of claim 1 wherein
R$_2$ is naphthylmethyl
X is halogen.
4. The process of claim 1 wherein
R$_2$ is benzyl, and
X is halogen.
5. The process of claim 4 wherein
R$_1$ and R$_1$' are methyl, and
X is chlorine.
6. A process for the preparation of a 1-substituted 1H-tetrazole-5-thiol of the formula:

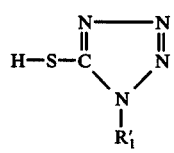 (I)

which comprises reacting at elevated temperature a substituted thiosemicarbazide of the formula:

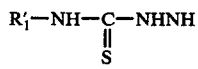 (II)

with a compound of the formula:

R$_2$—X  (III)

to give a N,S-disubstituted thiosemicarbazine of the formula:

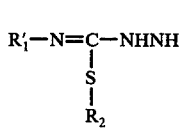 (IV)

subjecting at lower temperature the resultant compound (IV) to diazotization to give a 5-aralkylthio-1H-tetrazole of the formula:

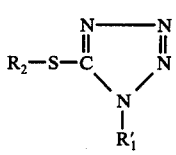 (V)

and reacting at elevated temperature the resultant compound (V) with a slightly molar excess of Friedel Crafts' catalyst to give a compound of the formula:

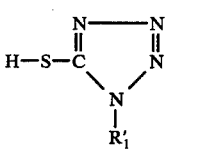 (I')

and when desired, converting the resultant compound (I') into its salt, wherein
R$_1$' is cycloalkyl of 5–6 carbon atoms
R$_2$ is aralkyl, and
X is a residue of an acid.
7. A process for the preparation of a 1-substituted 1H-tetrazole-5-thio of the formula:

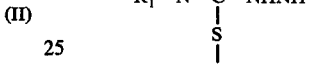 (I)

which comprises reacting at elevated temperature a substituted thiosemicarbazide of the formula:

R$_1$'—NH—C—NHNH  (II)
         ‖
         S with a compound of the formula:

R$_2$—X  (III)

to give a N,S-disubstituted thiosemicarbazine of the formula:

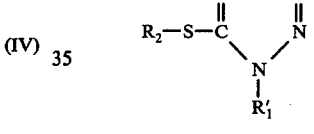 (IV)

subjecting at lower temperature the resultant compound (IV) to diazotization to give a 5-aralkylthio-1H-tetrazole of the formula:

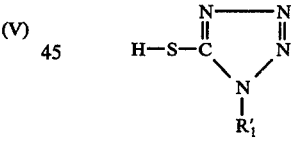 (V)

and reacting at elevated temperature the resultant compound (V) with a slightly molar excess of Friedel Crafts' catalyst to give a compound of the formula:

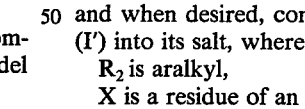 (I')

and when desired, converting the resultant compound (I') into its salt, wherein
R$_2$ is aralkyl,
X is a residue of an acid, and
R$_1$' is acylaminoalkyl wherein alkyl is of 1–6 carbon atoms, and acyl is alkanoyl of 1–7 carbon atoms, benzoyl, toluoyl, xyloyl, nicotinoyl, thenoyl or furoyl
and, when desired, followed by hydrolyzing the resultant compound (I') to give a compound of the formula:

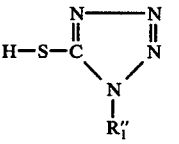 (I")

and further, when desired, followed by reacting the resultant compound (I'') with a reagent being capable of introducing an alkoxycarbonyl group on the amino group to give a compound of the formula:
and furthermore, when desired, converting the resultant compound (I'), (I'') or (I''') into its salt.
* * * * *